US011144322B2

(12) United States Patent
Feng et al.

(10) Patent No.: US 11,144,322 B2
(45) Date of Patent: Oct. 12, 2021

(54) CODE AND DATA SHARING AMONG MULTIPLE INDEPENDENT PROCESSORS

(71) Applicant: MediaTek Inc., Hsinchu (TW)

(72) Inventors: Hsiao Tzu Feng, Hsinchu (TW);
Chia-Wei Chang, Hsinchu (TW);
Li-San Yao, Hsinchu (TW)

(73) Assignee: MediaTek Inc., Hsinchu (TW)

( * ) Notice: Subject to any disclaimer, the term of this patent is extended or adjusted under 35 U.S.C. 154(b) by 35 days.

(21) Appl. No.: 16/675,212

(22) Filed: Nov. 5, 2019

(65) Prior Publication Data
US 2021/0132952 A1 May 6, 2021

(51) Int. Cl.
*G06F 9/445* (2018.01)
*G06F 12/0875* (2016.01)
*G06F 9/38* (2018.01)
*G06F 9/30* (2018.01)
*G06F 9/48* (2006.01)

(52) U.S. Cl.
CPC ........ *G06F 9/3836* (2013.01); *G06F 12/0875* (2013.01); *G06F 9/3004* (2013.01); *G06F 9/44557* (2013.01); *G06F 9/44563* (2013.01); *G06F 9/4881* (2013.01); *G06F 2212/452* (2013.01)

(58) Field of Classification Search
CPC ...... G06F 9/3836; G06F 9/3004; G06F 9/445; G06F 9/44563; G06F 9/44557; G06F 9/4881; G06F 12/0848; G06F 12/0875; G06F 2212/452; G06F 8/66

USPC .......... 712/30, 203, 230, 245, 248; 711/121, 711/123, 129, 147, 153, 173
See application file for complete search history.

(56) References Cited

U.S. PATENT DOCUMENTS

| | | | | |
|---|---|---|---|---|
| 6,813,522 | B1* | 11/2004 | Schwarm | G06F 9/4405 700/5 |
| 2003/0221080 | A1* | 11/2003 | Sexton | G06F 9/445 711/170 |
| 2010/0332771 | A1* | 12/2010 | Gray | G06F 12/0835 711/148 |
| 2015/0286573 | A1* | 10/2015 | Socarras | G06F 11/2236 711/123 |
| 2018/0165133 | A1* | 6/2018 | Iyigun | G06F 12/1036 |

* cited by examiner

*Primary Examiner* — Daniel H Pan
(74) *Attorney, Agent, or Firm* — Tong J. Lee

(57) ABSTRACT

A system includes a memory and multiple processors. The memory further includes a shared section and a non-shared section. The processors further include at least a first processor and a second processor, both of which read-only access to the shared section of the memory. The first processor and the second processor are operable to execute shared code stored in the shared section of the memory, and execute non-shared code stored in a first sub-section and a second sub-section of the non-shared section, respectively. The first processor and the second processor execute the share code according to a first scheduler and a second scheduler, respectively. The first scheduler operates independently of the second scheduler.

18 Claims, 4 Drawing Sheets

CODE AND DATA SHARING AMONG MULTIPLE INDEPENDENT PROCESSORS

TECHNICAL FIELD

Embodiments of the invention relate to a multiprocessor computing system having shared access to at least a portion of a memory subsystem.

BACKGROUND

A modern computing system typically has multiple processors, each of which has its own dedicated memory. A mobile device system, such as a smartphone, generally provides limited memory capacity for its user due to its limited form factor. With the increased demand in storage of multimedia content, there is also an increased demand on the memory capacity. Increasing memory capacity contributes to increased power consumption due to leakage current, as well as increased cost due to higher gate count. Therefore, efficient usage of the existing memory capacity without adding more memory to a system can significantly improve the performance and cost of the system.

A number of approaches have been proposed for efficient memory usage. However, there is a need for developing a strategy specifically for a memory-constrained multiprocessor system.

SUMMARY

In one embodiment, a system is provided for code sharing. The system includes a memory and a plurality of processors. The memory further includes a shared section and a non-shared section. The processors further include at least a first processor and a second processor, both of which read-only access to the shared section of the memory. The first processor and the second processor are operable to execute shared code stored in the shared section of the memory, and execute non-shared code stored in a first sub-section and a second sub-section of the non-shared section, respectively. The first processor and the second processor execute the share code according to a first scheduler and a second scheduler, respectively. The first scheduler operates independently of the second scheduler.

In another embodiment, a method is provided for code sharing among a plurality of processors. The method comprises: storing shared code in a shared section of a memory and non-shared code in a non-shared section of the memory; executing, by a first processor according to a first scheduler, the shared code in the shared section; and executing, by a second processor according to a second scheduler, the shared code in the shared section. The first processor and the second processor have read-only access to the shared section, and the second scheduler operates independently of the first scheduler.

Other aspects and features will become apparent to those ordinarily skilled in the art upon review of the following description of specific embodiments in conjunction with the accompanying figures.

BRIEF DESCRIPTION OF THE DRAWINGS

The present invention is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one. Further, when a particular feature, structure, or characteristic is described in connection with an embodiment, it is submitted that it is within the knowledge of one skilled in the art to effect such feature, structure, or characteristic in connection with other embodiments whether or not explicitly described.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description. It will be appreciated, however, by one skilled in the art, that the invention may be practiced without such specific details. Those of ordinary skill in the art, with the included descriptions, will be able to implement appropriate functionality without undue experimentation.

Embodiments of the invention provide a system and method for sharing executable code in a memory accessible by multiple processors. Read-only data in the memory may also be shared among the processors. The processors execute instructions according to their respective independent schedulers. The processors execute the shared code without copying the shared code into their respective non-shared sub-sections of the memory. Thus, the amount of memory occupied by the shared code and data can be significantly reduced, which, in turn, reduces the demand for memory capacity in a device. The amount of memory in a device is directly proportional to the gate count, leakage current and cost of the device. As such, the code and data sharing described herein can improve the efficient usage of the memory and, therefore, the performance and cost of a device containing the memory.

Figure 1:
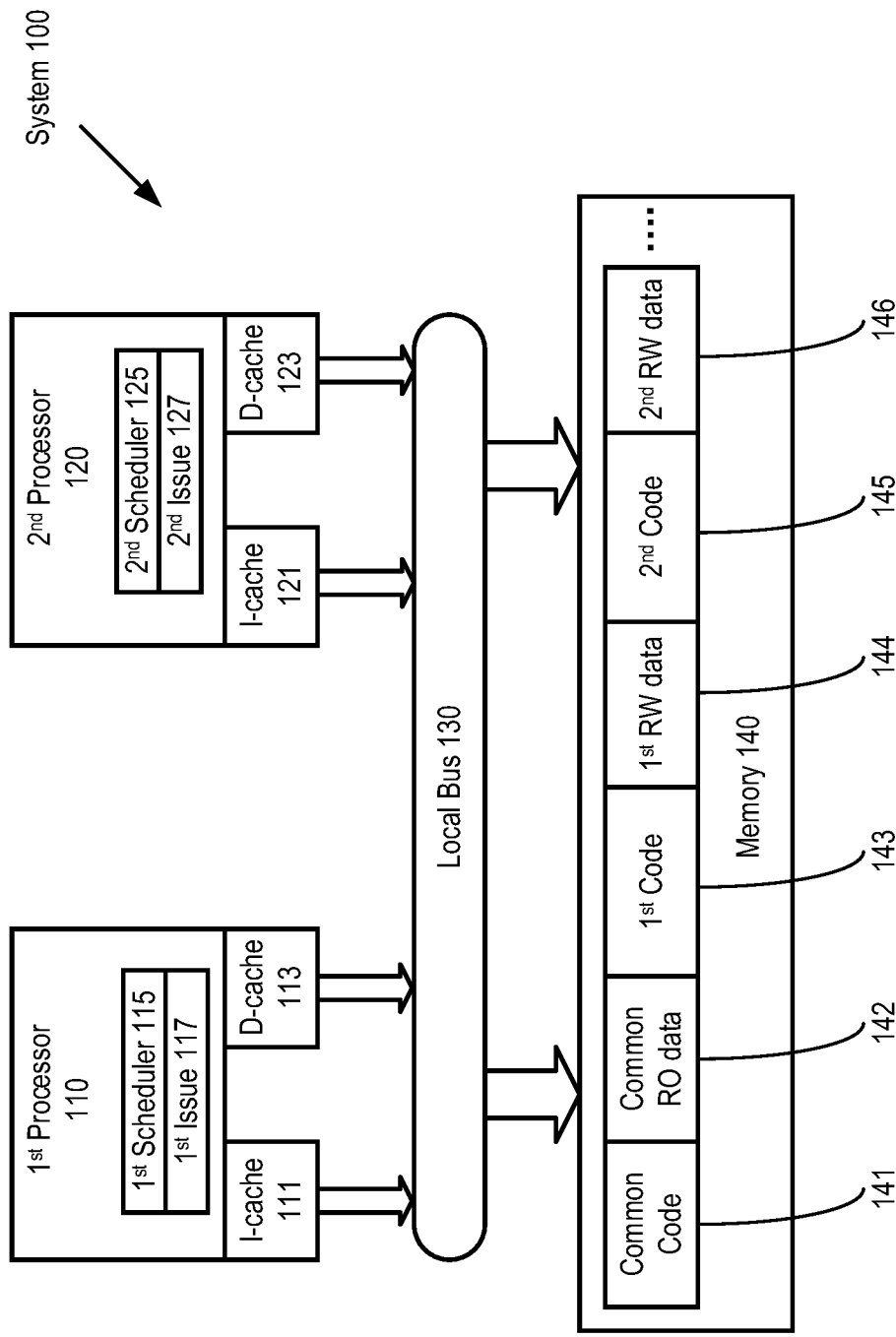
FIG. 1 illustrates a system in which embodiments of the invention may operate.

FIG. 1 is a block diagram illustrating a system 100 according to one embodiment. The system 100 includes two or more processors such as a first processor 110 and a second processor 120. In some embodiments, a processor may be referred to as a processor core, a microprocessor, a core, a multi-core processor, a computing unit, an execution unit, processing circuitry, or the like. The following description uses two processors as an example; however, it is understood that the description is applicable to more than two processors sharing access to the same memory.

The first processor 110 and the second processor 120 may have the same or compatible Instruction Set Architecture (ISA), which enables them to execute instructions from the same or compatible instruction set. In some embodiments, the processors 110 and 120 may have different microarchitecture in the implementation of the same or compatible ISA. An example of compatible ISA may include the ISA of the same processor architecture series, such as the RISC-V® series, the Arm® series, the MIPS® series, or other processor architecture series.

In one embodiment, the first processor 110 and the second processor 120 execute instructions according to the tasks scheduled by their schedulers 115 and 125, respectively. A task includes a set of instructions. The schedulers 115 and 125 operate independently of each other; for example, the schedulers 115 and 125 may schedule different tasks for their respective processors to execute at a given time. Scheduled instructions may be issued when they are ready for execution. The first processor 110 and the second processor 120 also include respective issue circuitry (i.e., a first issue circuitry 117 and a second issue circuitry 127). The first issue circuitry 117 and the second issue circuitry 127 also operate independently of each other. Furthermore, the processors 110 and 120 operate independently; more specifically, by receiving tasks and instructions from their respective schedulers 115 and 125 and respective issue circuitry 117 and 127. The processors 110 and 120 do not receive tasks or instructions from a centralized task scheduler and/or a centralized instruction issue circuitry. In other words, the processors 110 and 120 can execute instructions (e.g., user and operating system instructions) independent of each other.

Each of the first processor 110 and the second processor 120 is coupled to a set of cache memory; e.g., an instruction cache (I-cache 111 or 121) and a data cache (D-cache 113 or 123). The cache memory may be used to store pre-fetched instructions and frequently-used data to reduce delay in accessing the memory 140. In one embodiment, the I-caches 111 and 121 may store instructions that are expected to be executed repeatedly, such as instructions in a while-loop. In one embodiment, the first processor 110, the second processor 120, and their respective cache memory may be part of a System-on-a-Chip (SoC) platform. In one embodiment, the SoC platform may be part of a mobile computing and/or communication device, a desktop computing system, a server computing system, a cloud computing system, or the like.

In one embodiment, the first processor 110 and the second processor 120 have shared memory access to a memory 140. The memory 140 may be the system memory or the main memory of the system 100. The memory 140 may include Random Access Memory (RAM) devices such as a Dynamic Random Access Memory (DRAM) device, a flash memory device and/or other volatile or non-volatile memory devices. The memory 140 may also include read-only memory (ROM) for storing read-only data or read-only code (e.g., shared code). The first processor 110 and the second processor 120 may access the memory 140 via a local bus 130 or another type of connection.

In one embodiment, the memory 140 includes a shared section and a non-shared section. For example, the shared section may include a common code region 141 and a common read-only (RO) data region 142. The shared section is write-protected (e.g., read-only) to ensure data integrity. The non-shared section may be partitioned into multiple sub-sections, with each sub-section allocated to one processor. For example, the first processor 110 is allocated with a first sub-section including a first code region 143 and a first read-and-write (RW) data region 144. The second processor 120 is allocated with a second sub-section including a second code region 145 and a second RW data region 146.

The common code region 141 stores programs shared by two or more processors. For example, a program that measures the elapsed time in execution may be shared by multiple processors. The first processor 110 and the second processor 120 execute the shared code in the common code region 141 independently of each other. Using the common code region 141 to store shared programs, without saving a copy of these programs in each non-shared sub-sections, can significantly save storage space in the memory 140. Similarly, the common RO data region 142 stores read-only data shared by two or more processors. For example, the shared data may include input parameters used by the shared programs stored in the common code region 141. Other shared read-only data may also be stored in the common RO data region 142. The use of the common RO data region 142 can also significantly save storage space in the memory 140.

In one embodiment, the processors 110 and 120 may concurrently, or at different times, read from the shared section of the memory 140 during program execution. The execution results may be written to their respective non-shared sub-sections.

The common code region 410 stores machine-executable instructions that can be executed by the processors 110 and 120. The machine-executable instructions may specify source operands (e.g., input data) and/or destination operands (e.g., execution results). For example, a source operand may be loaded from a given memory address in the shared section of the memory 140. In some cases, source operands and/or destination operands may be located in the non-shared section of the memory 140. In one embodiment, the first processor 110 and the second processor 120 may be provided with the same memory address or pointer when executing an instruction in the common code region 410. This memory address or pointer may point to a memory location at the first RW data region 144 accessible by the first processor 110 only. At runtime, this memory address or pointer may be mapped or re-directed to another memory location at the second RW data region 146 accessible by the second processor 120 only. The mapping or re-direction may be performed by software or hardware, the details of which will be provided below with reference to FIG. 2.

Figure 2:
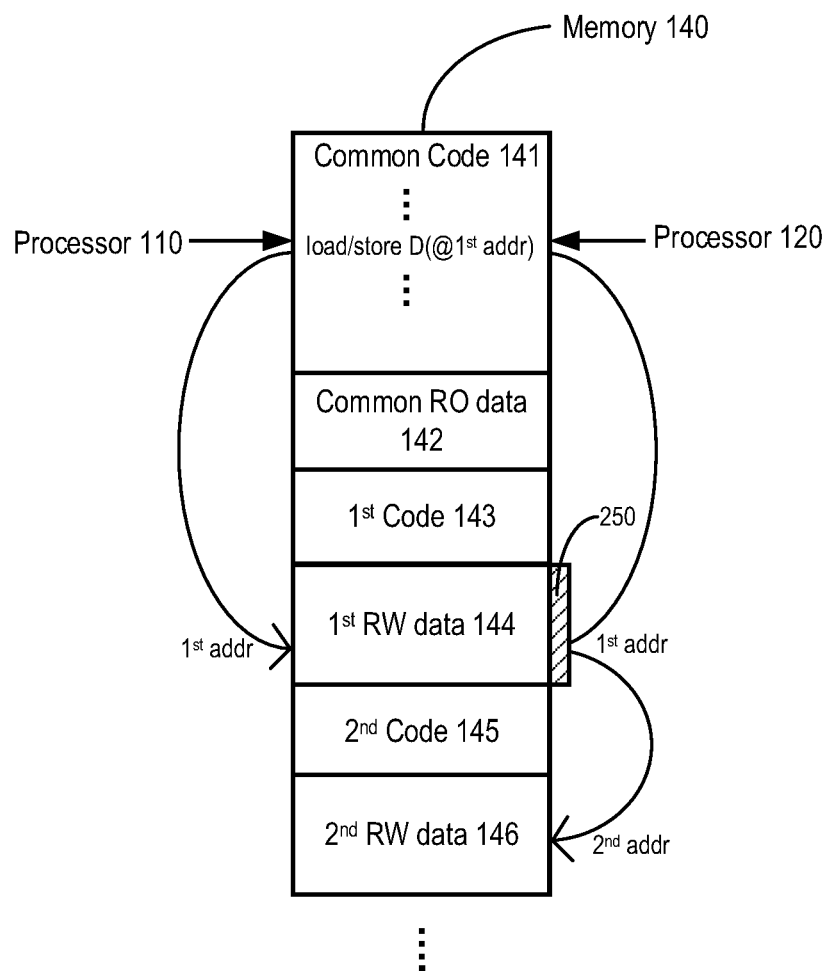
FIG. 2 is a diagram illustrating address mapping or re-direction according to one embodiment.

FIG. 2 is a diagram illustrating a memory operation, such as load or store, performed by the processors 110 and 120 according to one embodiment. When executing instructions stored in the common code region 141, the processors 110 and 120 may read data from the memory 140 and may generate execution results to be written back to the memory 140. In one embodiment, both of the processors 110 and 120 may execute, at the same time or at different times, a read/write (e.g., load/store) instruction having an operand at a first address in the first RW data region 144. The first processor 110 may read from or write to the first address, while the second processor 120 may read from or write to a second address mapped to the first address. In one embodiment, the second processor 120 may perform a method of address mapping at runtime as directed by memory management system software. In another embodiment, a hardware circuit 250, which may be coupled to the memory 140 and/or the second processor 120, is configured with an offset value. When the second processor 120 executes a read/write instruction having an operand at the first address, the hardware circuit 250 adds the offset value to the first address to generate a second address in the second sub-section, and re-directs the read/write operation of the second processor 120 from the first address to the second address.

In a system that includes additional processors (e.g., more than two), the hardware circuit 250 may be configured with a different offset value for each additional processor, such that the read/write access of these additional processors can also be re-directed to their respective non-shared sub-sections in the memory 140.

Figure 3:
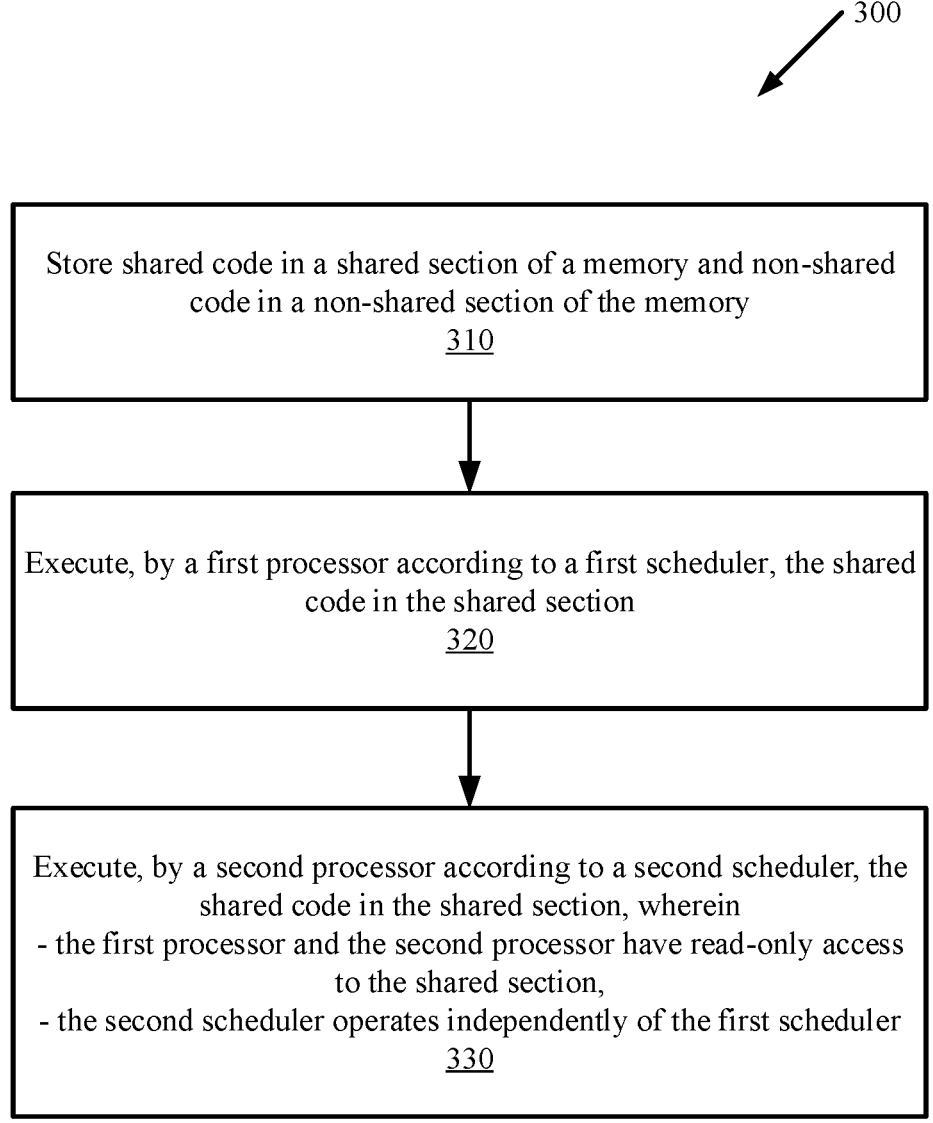
FIG. 3 is a flow diagram illustrating a method for code sharing according to one embodiment.

FIG. 3 illustrates a method 300 for code sharing according to one embodiment. The method 300 may be performed by the system 100 of FIG. 1 and/or the mobile device 400 of FIG. 4, or another computing and/or communication device.

In one embodiment, the device that performs the method 300 includes circuitry (e.g., processing hardware) and a machine-readable medium (e.g., memory) which stores instructions when executed cause the device to perform the method 300.

Referring to FIG. 3, in one embodiment, the method 300 begins at step 310 with storing shared code in a shared section of a memory, and non-shared code in a non-shared section of the memory. A first processor at step 320 executes, according to a first scheduler, the shared code in the shared section. A second processor at step 330 executes, according to a second scheduler, the shared code in the shared section. The first processor and the second processor have read-only access to the shared section. The second scheduler operates independently of the first scheduler.

In one embodiment, the device 100 and/or the mobile device 400 may include two or more processors sharing executable code in a shared section of the memory, without copying the shared code into their respective non-shared sub-sections. In one embodiment according to the shared code, the first processor and the second processor may execute a read/write instruction having an operand at a first address in the first sub-section, and at runtime the second processor may map the first address to a second address in the second sub-section according to an address mapping method. In another embodiment, a hardware circuit may at runtime re-directs the read/write operation performed by the second processor from the first address in the first sub-section to the second address in the second sub-section. In one embodiment, the first processor and the second processor may also share read-only data stored in the shared section of the memory.

Figure 4:
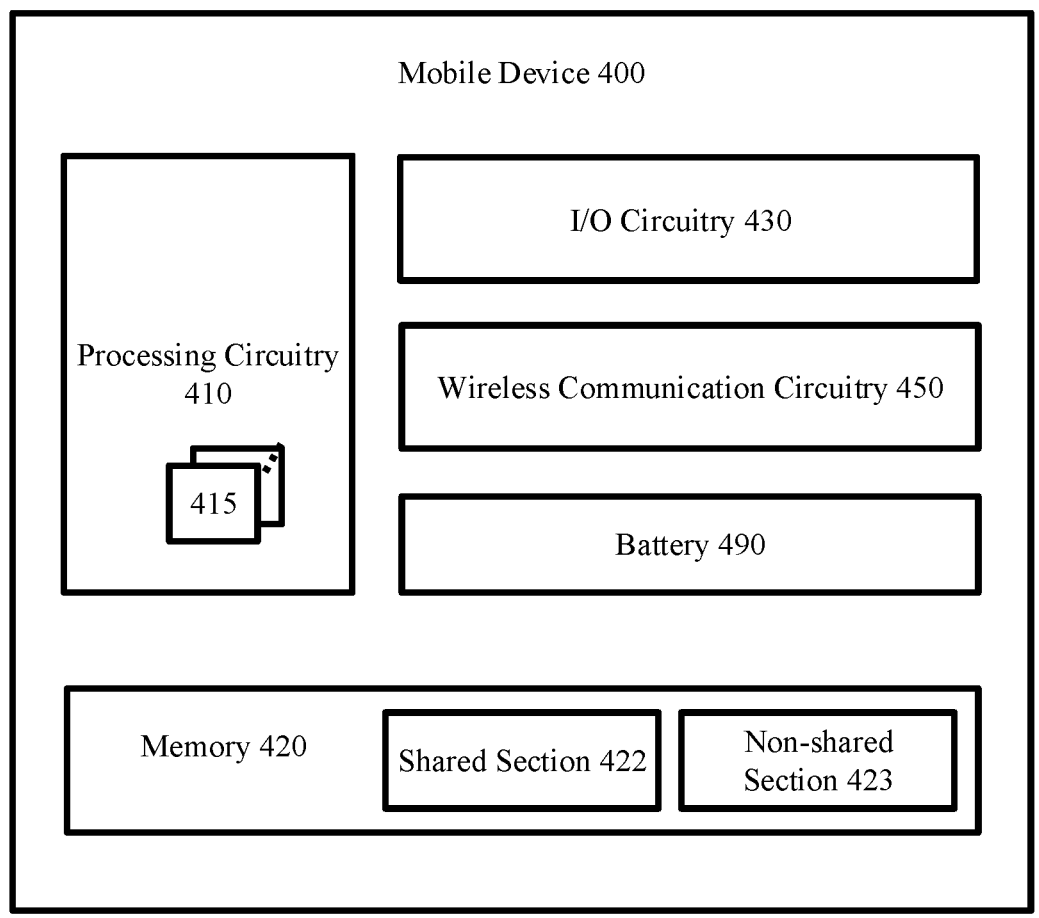
FIG. 4 illustrates an example of a mobile device according to one embodiment.

FIG. 4 illustrates an example of a mobile device 400 according to one embodiment. The mobile device 400 may be an example of the device 100 of FIG. 1, which provides a platform for the aforementioned video recording. The mobile device 400 includes processing circuitry 410, which further includes processors 415 (e.g., central processing units (CPUs), graphics processing units (GPUs), digital processing units (DSPs), multimedia processors, other general-purpose and/or special-purpose processing circuitry.). In some systems, the processor 415 may be the same as a "core" or "processor core," while in some other systems a processor may include multiple cores. Each processor 415 may include arithmetic and logic units (ALUs), control circuitry, cache memory, and other hardware circuitry. In one embodiment, the processing circuitry 410 is operative to execute software (including the aforementioned memory management system software) and applications that run on the mobile device 400. In one embodiment, the mobile device 400 is operative to perform the method 300 of FIG. 3.

The mobile device 400 further includes a memory 420 coupled to the processing circuitry 410. The memory 420 includes partitions such as a shared section 422 and a non-shared section 423. The memory 420 may include memory devices such as a dynamic RAM (DRAM) device, a ROM device, a flash memory device, and/or other volatile or non-volatile memory devices. The memory 420 may further include storage devices, for example, any type of solid-state or magnetic storage device. In one embodiment, the memory 420 may be the main memory or system memory of the mobile device 400.

The mobile device 400 may also include I/O circuitry 430 to receive input and display output. The I/O circuitry 430 may further include wireless communication circuitry 450, such as antennas, digital and/or analog radio frequency (RF) transceivers and RF circuitry. The mobile device 400 may further include a battery 490 to supply operating power to hardware components of the mobile device 400.

It is understood the embodiment of FIG. 4 is simplified for illustration purposes. Additional hardware components may be included, and some of the components shown in FIG. 4 may be omitted.

Although the mobile device 400 is used in this disclosure as an example, it is understood that the methodology described herein is applicable to any computing and/or communication device that includes multiple processors. Non-limiting examples of the mobile device 400 include a smartphone, a smartwatch, a wearable device, a tablet, a network-connected device, a gaming device, a navigation device, an Internet-of-Things (IoT) device, a graphics processing device, an infotainment device, an e-reader device, and other portable and/or wearable electronic devices.

The operations of the flow diagram of FIG. 3 have been described with reference to the exemplary embodiments of FIGS. 1 and 4. However, it should be understood that the operations of the flow diagram of FIG. 3 can be performed by embodiments of the invention other than the embodiments of FIGS. 1 and 4, and the embodiments of FIGS. 1 and 4 can perform operations different than those discussed with reference to the flow diagrams. While the flow diagram of FIG. 3 shows a particular order of operations performed by certain embodiments of the invention, it should be understood that such order is exemplary (e.g., alternative embodiments may perform the operations in a different order, combine certain operations, overlap certain operations, etc.).

Various functional components or blocks have been described herein. As will be appreciated by persons skilled in the art, the functional blocks will preferably be implemented through circuits (either dedicated circuits, or general-purpose circuits, which operate under the control of one or more processors and coded instructions), which will typically comprise transistors that are configured in such a way as to control the operation of the circuitry in accordance with the functions and operations described herein.

While the invention has been described in terms of several embodiments, those skilled in the art will recognize that the invention is not limited to the embodiments described, and can be practiced with modification and alteration within the spirit and scope of the appended claims. The description is thus to be regarded as illustrative instead of limiting.

What is claimed is:

1. A system operative to share code, comprising:
 a memory including a shared section and a non-shared section; and
 a plurality of processors including at least a first processor and a second processor, the first processor and the second processor having read-only access to the shared section of the memory, wherein the first processor and the second processor are operable to:
  execute shared code stored in the shared section of the memory according to a first scheduler and a second scheduler, respectively, wherein the first scheduler operates independently of the second scheduler,
  execute non-shared code stored in a first sub-section and a second sub-section of the non-shared section, respectively, and
  execute a read or write instruction having an operand at a first address in the first sub-section according to the shared code, and
 wherein, to access the operand, the second processor at runtime is further operable to map the first address to a second address in the second sub-section according to an address mapping method.

2. The system of claim 1, wherein the first processor and the second processor are further operable to write respective results of executing the shared code in the first sub-section and the second sub-section, respectively.

3. The system of claim 1, further comprising a hardware circuit which at runtime re-directs a read or write operation performed by the second processor from a first address in the first sub-section to the second address in the second sub-section.

4. The system of claim 1, wherein the first processor and the second processor are further operable to concurrently access the shared section of the memory.

5. The system of claim 1, wherein the first processor and the second processor are operative to share read-only data stored in the shared section of the memory.

6. The system of claim 1, wherein the first processor and the second processor execute the shared code independently of each other.

7. The system of claim 1, wherein the first processor and the second processor have a same or compatible instruction set architecture (ISA).

8. The system of claim 1, wherein the first processor and the second processor are operable to execute the shared code stored in the shared section without having a copy of the shared code in the non-shared section.

9. The system of claim 1, wherein the memory and the plurality of processors are encased in a mobile device.

10. A method for code sharing, comprising
storing shared code in a shared section of a memory and non-shared code in a non-shared section of the memory, the non-shared section including a first sub-section and a second sub-section;
executing, by a first processor according to a first scheduler, the shared code in the shared section and the non-shared code in a first sub-section of the non-shared section;
executing, by a second processor according to a second scheduler, the shared code in the shared section and the non-shared code in a second sub-section of the non-shared section;
executing, by the first processor and the second processor, a read or write instruction having an operand at a first address in the first sub-section according to the shared code; and
mapping, by the second processor at runtime, the first address to a second address in the second sub-section to access the operand according to an address mapping method,
wherein the first processor and the second processor have read-only access to the shared section, and the second scheduler operates independently of the first scheduler.

11. The method of claim 10, further comprising:
writing first results of executing the shared code in the first sub-section by the first processor; and
writing second results of executing the shared code in the second sub-section by the second processor.

12. The method of claim 10, further comprising:
re-directing, by a hardware circuit, a read or write operation performed by the second processor from a first address in the first sub-section to the second address in the second sub-section.

13. The method of claim 10, further comprising:
accessing, by the first processor and the second processor, the shared section of the memory concurrently.

14. The method of claim 10, further comprising:
sharing, by the first processor and the second processor, read-only data stored in the shared section of the memory.

15. The method of claim 10, wherein the first processor and the second processor execute the shared code independently of each other.

16. The method of claim 10, wherein the first processor and the second processor have a same or compatible instruction set architecture (ISA).

17. The method of claim 10, further comprising:
executing the shared code in the shared section without copying the shared code into the non-shared section.

18. The method of claim 10, wherein the memory, the first processor and the second processor are encased in a mobile device.

* * * * *